(12) United States Patent
Herskovic

(10) Patent No.: US 10,773,099 B2
(45) Date of Patent: Sep. 15, 2020

(54) CORRUGATED STENT

(71) Applicant: Arnold M. Herskovic, Chicago, IL (US)

(72) Inventor: Arnold M. Herskovic, Chicago, IL (US)

( * ) Notice: Subject to any disclaimer, the term of this patent is extended or adjusted under 35 U.S.C. 154(b) by 0 days.

(21) Appl. No.: 16/277,380

(22) Filed: Feb. 15, 2019

(65) Prior Publication Data
US 2020/0261741 A1 Aug. 20, 2020

(51) Int. Cl.
*A61N 5/00* (2006.01)
*A61M 36/00* (2006.01)
*A61M 36/04* (2006.01)
*A61M 36/12* (2006.01)
*A61N 5/10* (2006.01)

(52) U.S. Cl.
CPC .... *A61N 5/1007* (2013.01); *A61N 2005/1011* (2013.01); *A61N 2005/1025* (2013.01)

(58) Field of Classification Search
CPC .................. A61N 5/1001; A61N 17/12118
See application file for complete search history.

(56) References Cited

U.S. PATENT DOCUMENTS

| 5,282,847 | A | 2/1994 | Trescony |
| 6,090,996 | A | 7/2000 | Li |
| 8,568,284 | B2 * | 10/2013 | White ................. A61N 5/1015 600/3 |
| 2004/0034405 | A1 | 2/2004 | Dickson |
| 2014/0066896 | A1 * | 3/2014 | Tilson ............... A61M 25/1034 604/509 |

* cited by examiner

*Primary Examiner* — Christine H Matthews
*Assistant Examiner* — Joshua Daryl D Lannu
(74) *Attorney, Agent, or Firm* — Cherskov Flaynick & Gurda, LLC

(57) ABSTRACT

A material for brachytherapy is provided comprising a substrate having a longitudinal axis and a latitudinal, wherein the substrate comprises alternating peaks and valleys which are parallel to the longitudinal axis, the alternating peaks and valleys defining latitudinally extending pleats; and a plurality of medicament moieties positioned on the peaks and valleys of the substrate.

11 Claims, 8 Drawing Sheets

CORRUGATED STENT

FIELD OF INVENTION

The present invention relates to a device and method for delivering medicaments and more particularly, the present invention relates to a device and a method for treating cancers and tumors with radiation.

BACKGROUND

Some cancers and neoplasms are easier to treat with radiation than others. Hard-to-reach and and/or remove neoplasms, such as those in the esophagus, intestines and other lumens, are often treated via Brachytherapy. Brachytheraphy uses radioactive isotopes (commonly employed as seeds) to minimize radiation to adjacent, healthy tissue.

The radiation (dose distribution) depends on geometry especially the inverse square law, filtration by encapsulation material, and also adsorption in tissue and air. Individual seeds are shielded by the encapsulation process which usually limits the useful exposure to a short range of x- or gamma-rays. The initial dose rate would vary inversely with half-life. As an example, the typical initial dose rate for an Iodine 125 prostate implant would usually be about 0.07 Gy/hr (7 rad per hour as opposed to about 20 for Palladium 103. Host factors such as oxygenation, intrinsic radio sensitivity, proliferation rate, and repair capacity are more difficult to control.

Brachytherapy delivers radiation to small tissue volumes while limiting exposure of healthy tissue. In this regard, the delivered radiation conforms more to the target than any other form of radiation, (including proton therapy) as less normal transient tissue is treated. It features placement of radiation sources, such as small radioactive particles (usually as encapsulated seeds directly or in tubes or needles) near or within the target tissue, thus having the advantage over External Beam Radiation Therapy (EBRT) of being more focalized and less damaging to surrounding healthy tissue.

Brachytherapy is a common treatment for esophageal, prostate, and other cancers. Approximately 15,000 and 480,000 cases of esophageal cancer are diagnosed in the U.S. and worldwide, respectively. At least 50 percent of patients fail locally who present with curable cancers, which is to say that 50 percent suffer from persistence or recurrence of the cancers at the original cancer site. (Esophageal cancer treatment is a reasonable prototype for luminal brachytherapy that could be expanded to other sites.)

Brachytherapy can be delivered in several rates: a Low-Dose Rate (LDR, or less than 2 Gy/hr), a High-Dose Rate (HDR or greater than 12 Gy/hr), and a very Low Dose Rate vLDR. There is a Medium Dose Rate or hybrid at 2-12 gy/hr. The rates are expressed in Grays (Gy)/hour which are SI units of energy absorbed from ionizing radiation, equal to the absorption of one joule of radiation energy by one kilogram of matter. Since the inception of brachytherapy at the beginning of the $20^{th}$ century (i.e., soon after the discovery of radiation) delivery has been predominately LDR.

LDR brachytherapy typically delivers radiation at a rate of about 40 to 50 cGy/hr (e.g., 0.4 Gy/hr) while HDR typically delivers at a rate of about 0.2 Gy/minute. The instantaneous rate is much higher at each dwell location for HDR brachytherapy as the very active source must traverse the various treatment locations during each treatment.

LDR brachytherapy delivers radiation continuously (as prescribed relatively uniformly throughout the implanted volume), while HDR brachytherapy delivers radiation intermittently over several days. Regardless of the dose rate, a total final dosage of 60 Gy or less is usually delivered to the patient during LDR brachytherapy if it is the sole source of radiotherapy, and a total dose of 20-40 Gy is delivered during brachytherapy when used in combination with other forms of radiation treatment. These scenarios involve temporary implants in which the device is removed after completion of treatment. Very low dose radiation (vLDR) applicators can be used as LDR sources.

Brachytherapy has been used for more than half a century to treat prostate cancer. In this situation, low activity material emitting a low energy is placed next to or within a tumor. Until now these low emitting devices have mostly been left in place permanently except in extraordinary circumstances. The most commonly employed vLDR source (also known as permanent seeds) is Iodine-125 ($^{125}$I). $^{125}$I decays at a low energy radiation of 30 keV and emits radiation at a dose rate of about 0.04-0.1 Gy/hr (4 to 10 cGy/hr) continuously, up to a nominal year. vLDR is commonly used for cancers in which the radiation source can be placed proximate to or in the neoplasm and left for a significant period of time or permanently, such as when radioactive material or seeds are placed in prostate tumors.

Clinicians administer HDR brachytherapy in multiple sessions to improve patient tolerance. Thus, the patient is subjected to the additional risk of multiple procedures, often requiring anesthesia. Patients with cancers within lumen, ducts, or tracts, such as cancer of the esophagus or biliary tract of the liver, have less tolerance for brachytherapy if connections (for example, catheters) are connected externally for multiple days. Such protracted use of catheters often leads to kinking, dislodgement, obstruction, irritation, and the risk of life-threatening infections. (The most commonly employed HDR radio isotopic source is Ir 192 with an energy of 0.38 MEV and half live of 74 days. Cs 137 (T1/2 30.2 years energy 0.662 MEV and Co 60 T1/2 5 years and energy of 1.2 MEV have occasionally been used.)

HDR employs a primary housing containing a relatively high energy source (about 10 Ci), often as Iridium-192 (0.4 MeV). Treatment sessions last about 30 minutes. HDR is commonly applied in 2 to 3 daily sessions over the course of a few days, or multiple placement of an after-loading catheter in e.g. esophageal cancer treatment with multiple procedures and anesthesia.

Brachytherapy dosage is usually calculated at a fixed distance (or as a volume measuring the MPD or minimal peripheral dose) from the radiation source. HDR requires a highly active source delivering radiation at a dose rate of about 12 to 20 Gy/hr. Hot and cold spots, due to uneven distribution of radiation dose, occur with small deviations in distance between the tissue and the radiation source. Thus, brachytherapy treatment using a centralized radioactive material housing or containment can result in significant patient toxicity if the radioactive source is too close to normal or target tissues. For example, for patients with esophagus cancer, potentially life-threatening fistulas and hemorrhages occurred at a rate of 12 percent when treated with HDR brachytherapy in the study of Gasper et al, *International Journal of Radiation Oncology, Biology, Physics* 38 (1) 127-321 (1997). However, there are many reasons for the source to be skewed to one side as even an active tumor could displace the source. Lastly, HDR treatment requires a specially shielded patient room with appropriate radiation precautions. The vLDR applications disclosed in the instant specification do not.

State of the art devices for delivering radiation to internal tissues lack two important essential features: 1) the ability to remove or replace the radiation sources in situ when clinically appropriate, and 2) the ability to change the geometry, energy or radioactive sources of the radioactive particles or seeds in situ according to clinical needs. Typically, once the radiation source carrier(s) and the radiation source(s) is/are placed, they remain permanently within the patient or for the duration of patient treatment. Leaving a permanent radiation source in a patient, where it or its carrier may migrate over time or the tumor may change in shape or size, has the potential undesirable effect that healthy tissue will be exposed to the excessive radiation, while the target cancerous tissue is not. The ability to remove the radioactive sources in this situation or prior to surgery, while clinically useful, is currently lacking from the state of the art, as is the ability to easily localize the brachytherapy treatment or stent in vivo in the doctor's office without requiring formal imaging. In the event of a patient's death, it also may be desirable to remove the sources before cremation or burial.

Additionally, it may be clinically necessary to continue radiation therapy after the activity of the radioactive material has decayed. For example, $^{125}I$ has a half-life of about 60 days. If the tumor is still present or grows in size after an initial brachytherapy treatment (which sometimes occurs within six months), then it would be advantageous to replace the depleted radiation source with a source that has higher activity, a shorter half-life, that covers a longer length treatment site, or is marginally located. This is because new, perhaps faster growing, tumors may be better controlled with radiation that has a shorter half-life or that decays and emits radiation faster. Surviving tumor clones may have different biology and require faster or even slower radiation exposure rates for sterilization.

Approximately ninety percent of tumor recurrences occur where the original tumor was abutting healthy tissue. However, state of the art methods for delivering radiation at these margin areas after tumor excision have drawbacks. For example, radioactive seed-carrying sutures are sometimes used with absorbable mesh to close up excision sites. But the suture positions shift in time and the mesh may be absorbed by the body. This often leads to the sutures sometimes collapsing on themselves, and otherwise not maintaining the optimal seed positioning relative to the neoplasm or vulnerable tissue. Under-dosing occurs, which can lead to recurrence. Conversely, over dosing occurs, leading to injury to healthy tissue.

It would be advantageous to adjust the position and the activity of the radioactive source on its carrier in response to changes in tumor shape and size, carrier position, and other relevant therapeutic factors. It also may be appropriate to remove the radiation sources before surgery or other intervention to reduce personnel exposure or damage/contamination to sensitive equipment. Finally, it may be clinically useful to load the radioactive sources sometime after the placement of the device. None of the state of the art addresses provides these features.

Therefore, a need exists in the art for a method and device to deliver radiation and other medicaments to a patient while maintaining the original shape and size of the pre-operative surgical site (e.g., post lumpectomy). The device could be made to mimic the natural feel and bulk of original tissue simultaneous with delivering low level or high level radiation doses. The device should allow for embedment of radioactive particles in a reversibly deformable carrier and post-surgical repositioning of the carrier.

SUMMARY OF THE INVENTION

An object of this invention is to provide a device and a method for delivery medicaments that overcomes many of the disadvantages of the prior art.

Another object of the invention is to provide a device to enable focalized delivery of radiation in patients. A feature of this device is a medicament source supported by a reversibly deformable carrier (RDC), or a reversibly deployable substrate that has a pleated configuration. An advantage of the device is that it can accommodate body lumens that regularly change in size by providing a reversibly expandable and contractible scaffolding to support medicaments.

Still another object of the instant invention is to provide a method and device for delivering medicaments to a specific site in the body. A feature of the method and device is that a carrier used to support the medicaments expands or contracts to provide correct proximity of radioactive seeds to diseased parenchyma, perhaps even contacting the diseased tissue. This expansion may occur in vivo. For instance, a sheet embodying the invented configuration could be placed on the chest wall or peritoneal surfaces which could change in response to respiration, organ filling, or tumor shape changes. An advantage of the method and device is that it provides a means for allowing passage of ascetic-, pleural- and other-fluids through the device to contact surrounding tissue. This enables the eradication (destruction, killing, or deactivation) of floating tumor cells.

Yet another object of the invention is to provide a reversible deformable receiver for medicaments, wherein the receiver resides within a patient. A feature of the receiver is that it is adapted to support medicaments such as radioisotopes, therapeutic materials, pharmaceuticals, drugs, diagnostic materials, biologically active compounds or materials, or any other medicament, wherein the medicament resides on the outer surface of the receiver, concentrated at a specific region of the carrier, or else dispersed homogeneously throughout the carrier. An advantage of the invention is that the medicament may be applied locally in a focalized manner to target tissues. Another advantage is that the medicament receivers may be modified to facilitate medicament diffusion or movement from the receivers to target tissue once the carrier expands to contact the surfaces of the surgically produced void.

Briefly, the invention provides a material for brachytherapy comprising: a substrate having a longitudinal axis and a latitudinal axis, wherein the substrate comprises a plurality of generally flat panels connected to each other at alternating peaks and valleys which are parallel to the longitudinal axis, the alternating peaks and valleys defining latitudinally extending pleats; and a plurality of medicament moieties positioned on the peaks and valleys of the substrate.

The invention also provides a frustoconical shaped carrier of radioactive particles for use in in situ tumor treatment Also provided is a carrier of radioactive particles for brachytherapy, the carrier comprising a base defining a center region and a periphery; a plurality of leaves, each of said leaves defining a first proximal end hinge-ably attached to the periphery of the base, a second free distal end, and side edges extending from the first end to the second end; and radioactive seeds positioned along the side edges.

BRIEF DESCRIPTION OF THE DRAWINGS

The invention together with the above and other objects and advantages will be best understood from the following detailed description of the preferred embodiment of the invention shown in the accompanying drawings, wherein.

DETAILED DESCRIPTION OF THE INVENTION

Figure 1:
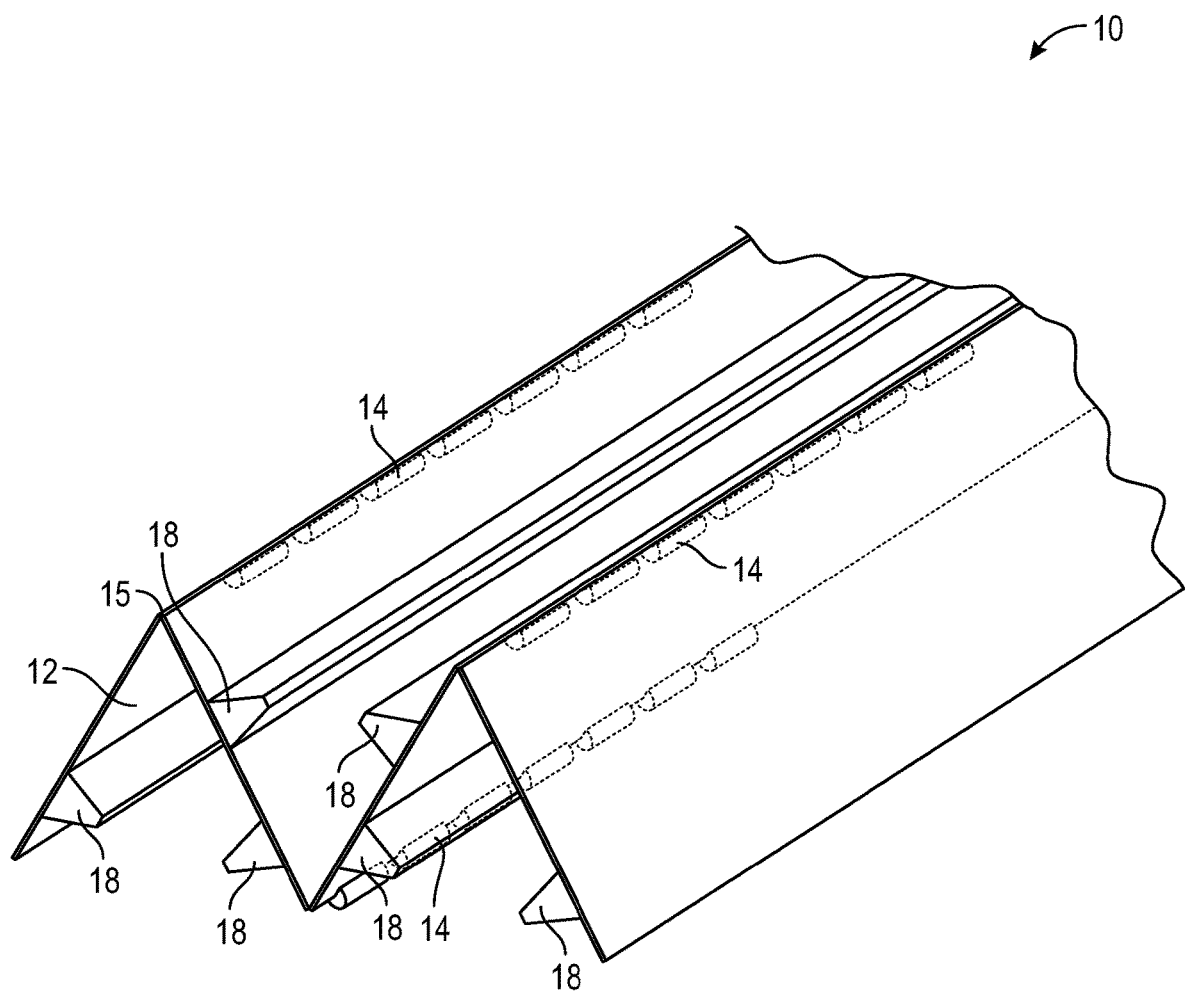
FIG. 1 is a perspective view of a pleated seed carrier in an un-deployed configuration in accordance with features of the present invention.

The foregoing summary, as well as the following detailed description of certain embodiments of the present invention, will be better understood when read in conjunction with the appended drawings.

As used herein, an element or step recited in the singular and preceded with the word "a" or "an" should be understood as not excluding plural said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

The invention provides a three dimensional vehicle for delivering and administering radiation in medical applications. The vehicle serves to either increase or decrease radiation dosage during course of treatment by varying the distance of radioactive seeds from target tissue in vivo.

Generally, the invented reversibly deployable device has the potential to improve treatment (for many cancers, hemodialysis shunts, fistulas and other injuries) by better preserving function, decreasing bleeding, providing palliation, and providing alternative treatments for applications in which surgery is the only available state of the art treatment.

The invention provides irradiated space fillers for cancer treatment, wherein the fillers offer palliation and minimally interfere with radiation or chemotherapy, while potentially decreasing patient toxicity and the incidence of fistulas.

Given the potential nonpermanent (i.e. changeable) shape of the carrier, carrier materials are chosen either to remain constant in volume so as to assure an accurate dose to tissue, or to expand or otherwise change shape in response to environmental stimuli, such as tumor shrinkage, temperature changes, contact with wavelength of certain frequencies, including visible light, ultra sound, laser radiation, heat, and combinations thereof.

The invented extendable stent accommodates body lumens that regularly change in size, such as the bladder that is constantly expanding and contracting. An embodiment of the invention is a corrugated substrate defining a series of pleats that can unfold to expand the radius of the stent to accommodate an expanded lumen. The stent supports brachytherapy sources, usually as seeds in the alternating peaks and valleys defined by the pleats of the stent. With this configuration of seeds, when the stent expands and the seeds in the valleys of the pleats move out of effective range, the seeds on the peaks of the pleats move in to effective range.

An embodiment of the invention comprises radiation sources (e.g., particles, seeds, wires, capsules potentially containing fluids, or other medicaments) embedded within the RDC, such as pleated substrates. The RDC, which can be shaped to conform to excision sites or lumen voids, provides spacing around the radiation sources. This embodiment prevents an infinitely high dose of radiation being applied to normal tissue. Thus, the invented configuration prevents accidents, such as burns, caused by high doses. Since there are 1.4 million cases of breast cancer detected annually, this is affordable, available treatment in areas in which care may be limited.

In another embodiment of the invention, single point source radiation particles are strung together or placed along the peaks and/or valleys of the pleated carrier. This embodiment is placed on a surface such as the pleura or peritoneum to treat malignancies involving those structures. To prevent bleeding in such applications, the carrier would be covered by an agent that promotes clotting, coagulation (i.e. thrombogenesis) and otherwise prevents bleeding. Alternatively, the carrier could be covered with a substance to promote a desired effect, such as antibiotics, anti-clotting material (to prevent adhesions), anti-tumor agents, growth- or other hormones, etc.

The invented device also decreases adverse toxicities (e.g. bleeding perforations, radiation-induced burns) otherwise caused by sub-optimum placement of the device. As such, the invention minimizes the creation of hotspots and fistulas to tissue, or failures due to cold spots.

The invention simultaneously allows for the carrier to contain medicament and the entire composite to expand or contract over time, given that vLDR radiation dosimetry is sensitive to geometric factors. Generally, the dose varies as the inverse square of the distance. With isotopes having higher energy, tissue attenuation is lower.

The carrier-medicament composites may be inserted through a needle or trocar into the desired site. While straight or curved needles may be utilized, straight needles may facilitate easier loading of medicament-composites comprising radioactive material intercalated with spacers as described infra. The pleated devices could be placed via endoscope or at open surgery as in breast lumpectomy.

An exemplary embodiment will be described in reference to FIG. 1 as numeral 10. As described supra, the device comprises an RDC 12 which supports medicament 14. The RDC is shown as a pleated substrate having a first side and a second side. The RDC is shown in FIG. 1 in a contracted or undeployed configuration. As such the un-deployed configuration defines two superior or peak regions 15, those regions extending in a direction orthogonal to the direction in which the pleat extends during deployment. Also shown is a valley portion 16. This valley portion 16 resides in a plane inferior to the plane containing both peak regions 15.

Each of the peaks 15 and valley 16 regions of the carrier support radioactive substrates 14. As such, the radioactive substrates 16 residing in the valley are positioned below the radioactive substrates supported on the ridges defining the peak regions 15. The seeds can be carriers (tubes) which are fixed to the pleated structures via glue, sutures, staples etc. Alternatively, the seeds are slidably and reversibly received by tubes fixed to the valleys and ridges of the substrate. These tubes may or may not be biodegradable and flexible.

The walls of a structure allow contraction or expansion in a single direction (e.g., a 1:2 ratio from a contracted to a fully deployed configuration). The radial dimension expansion/contraction occurs when the corrugated pleats over- or under-lap allowing for some filtration of the radioactive sources.

Figure 2:
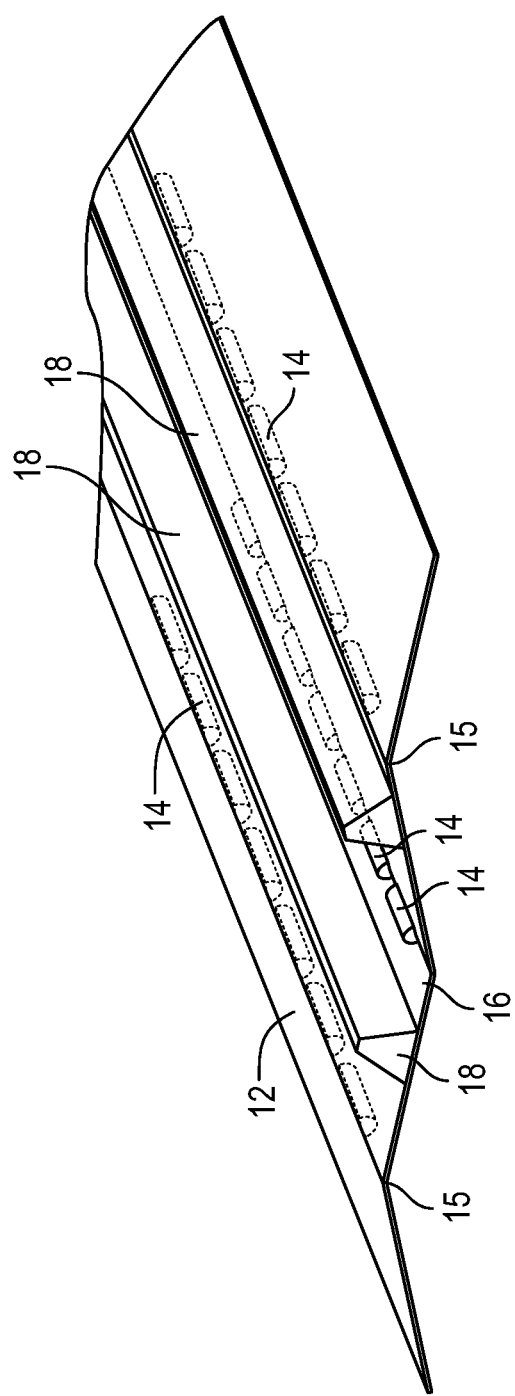
FIG. 2 is a perspective view of the pleated seed carrier of FIG. 1, but in a deployed configuration.

In an embodiment of the invention (and as shown in FIGS. 1 and 2), the side of the corrugated substrate to which the seeds are attached is opposite the side of the substrate directly opposing the mucosa. Therefore, the seed supporting side faces away from normal tissue mucosa. This provides a means for some filtration or attenuation of the radiation dose impinging upon the mucosa. Other attenuation means includes a shielding layer 13 (FIG. 6) overlying the bottom surface(s) 12b of the pleated substrate 12. This would shield collateral tissue proximal to the undersurface 12b, such collateral tissue being a blood vessel, a nerve, bone, etc.

Other embodiments have every other seed residing on opposite surfaces. Still other embodiments have all seeds residing on the surface of the device directly facing the mucosa. Also, seeds proximal to peak portions 15 of the device may reside on the surfaces as shown in FIGS. 1 and 2 which seeds proximal to the valley 16 may have seeds residing on the surface directly facing mucosa. Seed placement depends on the parenchyma and neoplasm involved.

Figure 9A:
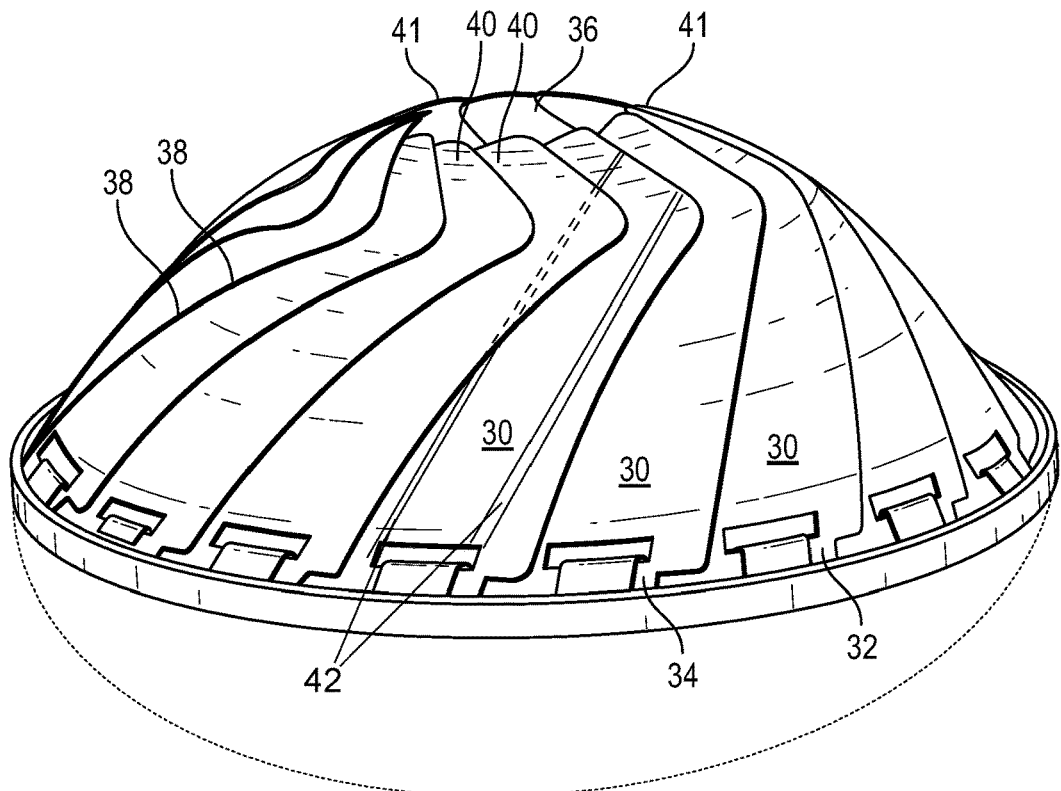
FIG. 9A is a perspective view of an isotope carrier in an un-deployed configuration, in accordance with features of the present invention.
Figure 9B:
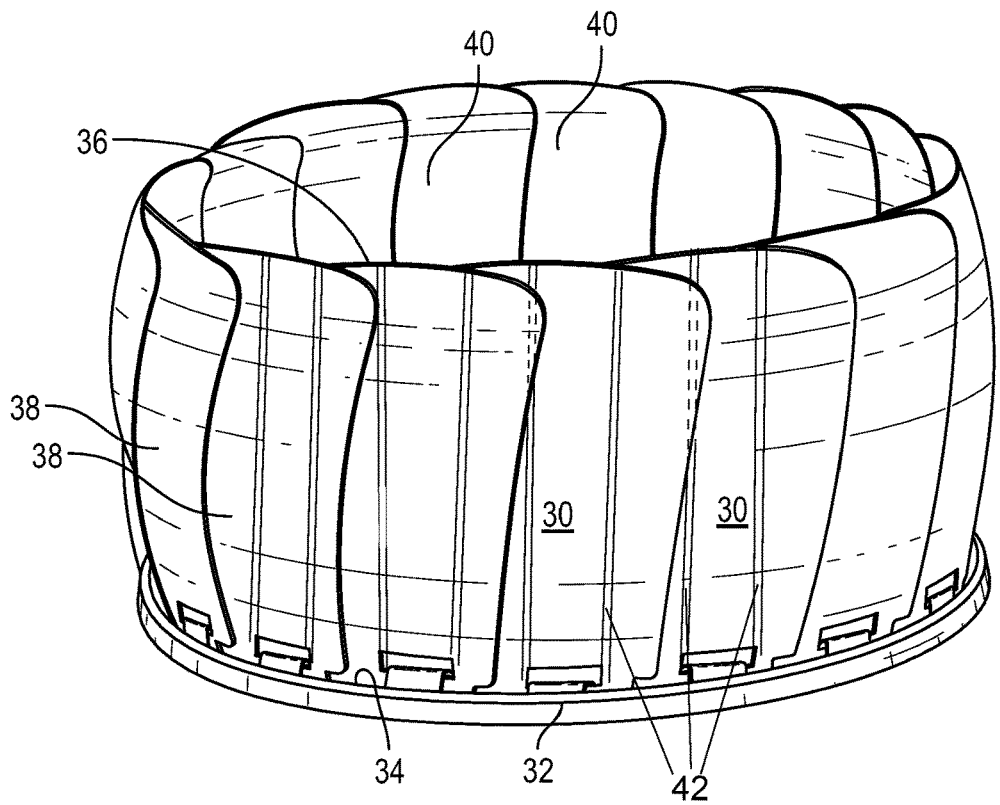
FIG. 9B is a perspective view of the isotope carrier of FIG. 9A in a semi-deployed configuration, in accordance with features of the present invention.
Figure 9C:
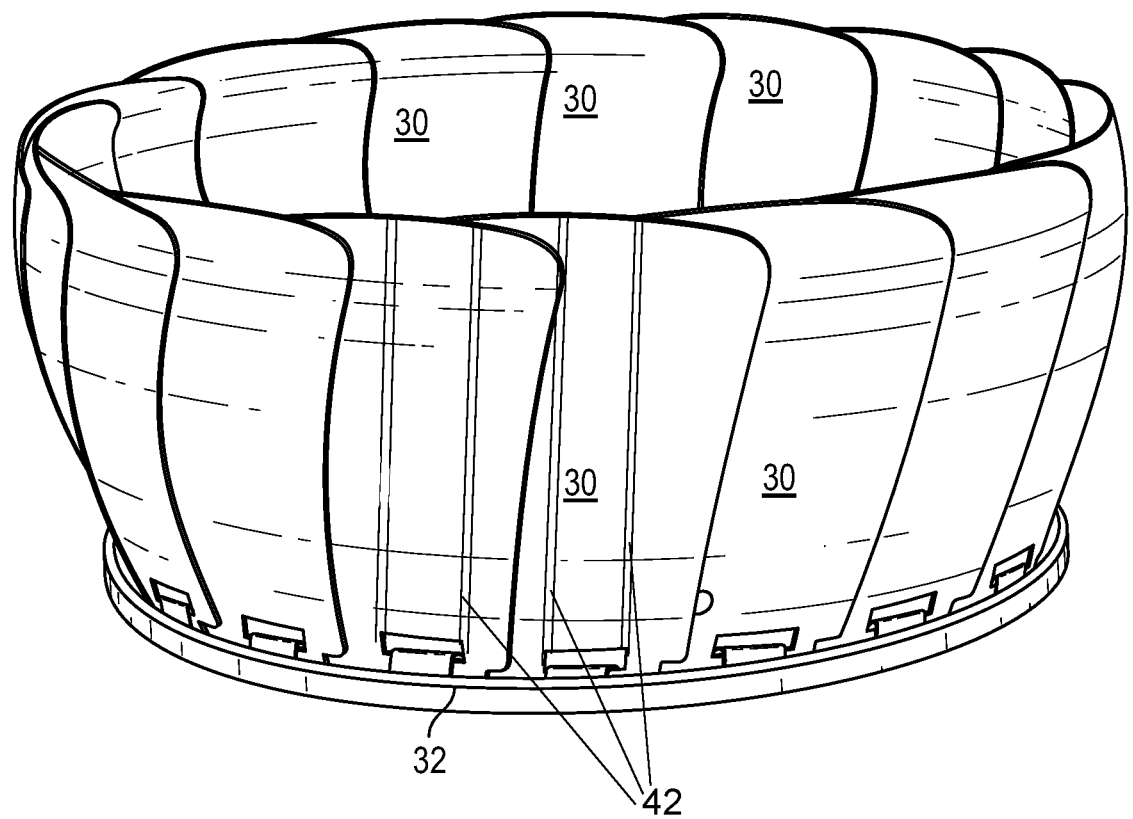
FIG. 9 C is a perspective view of the isotope carrier of FIG. 9A in a deployed configuration, in accordance with features of the present invention.

If a fully deployed substrate forms sections of a spherical body, then this feature enables the spheroid to expand both radially and along the axis, each potential approaching a 2:1 ratio. FIG. 9A-9C shows a top half of such a spherical body, with 9A depicting the top half of the sphere collapsed or un-deployed. The bottom half is depicted in phantom. FIG. 9B shows the top half of the sphere partially deployed or opened up. FIG. 9B shows the top half of the sphere completely opened. In some instances, the top half may be un-deployed, while the bottom half is fully deployed.

FIG. 2 shows the device 12 in deployment mode. As depicted, the radioactive substrates formerly residing in the valley 16 are now approximately in the same plane in which the radioactive substrates supported by the peaks reside. Each lane of medicament is approximately a centimeter apart from its adjacent lane. This results in approximately a 50 percent increase in radiation volume and associated dosage to neighboring tissue, such that three catheters are treating the mucosa instead of two. The middle catheter or lane may reside up to about 0.5 centimeters below the plane formed by the flanking portions "f" of the pleat. Initially, the seeds by be slidably received by catheters or sleeves so as to be contained in the catheters or sleeves. Then, the catheters are attached to the peaks and valleys. Further, this configuration results in a 100 percent increase in treatment surface, compared to when the carrier is folded (i.e., not expanded, so shown in FIG. 1).

Optionally, a bumper 18 or plurality of bumpers may be positioned on opposing surfaces of a pleat region. The bumpers may be simple protuberances, or alternatively, the bumpers may extend substantially the entire length of the substrate so as to be parallel to the peaks and/or valleys.

These bumpers serve two functions: In the collapsed configuration (FIG. 1) the bumpers 18 assure that appropriate spacing is maintained between the two rows of radiation seeds. (In some embodiments, the seed rows of adjacent peaks may be more than approximately 1 cm apart.) Secondly, while the substrate 12 is in the collapsed configuration, the bumpers aid in attenuating radiation emanating from the seeds situated underneath the bumpers and along the valley between the peaks. The width of the bumpers may be approximately equal to the length of the peaks and/or valleys lined with the seeds, where the length is determined by the number of seeds placed along the peaks and/or valleys. When the substrate 12 is expanded to a configuration resembling FIG. 2, the attenuation function of the bumpers is minimized. If the substrate 12 is partially expanded, some attenuation by the bumpers may occur.

Figure 7:
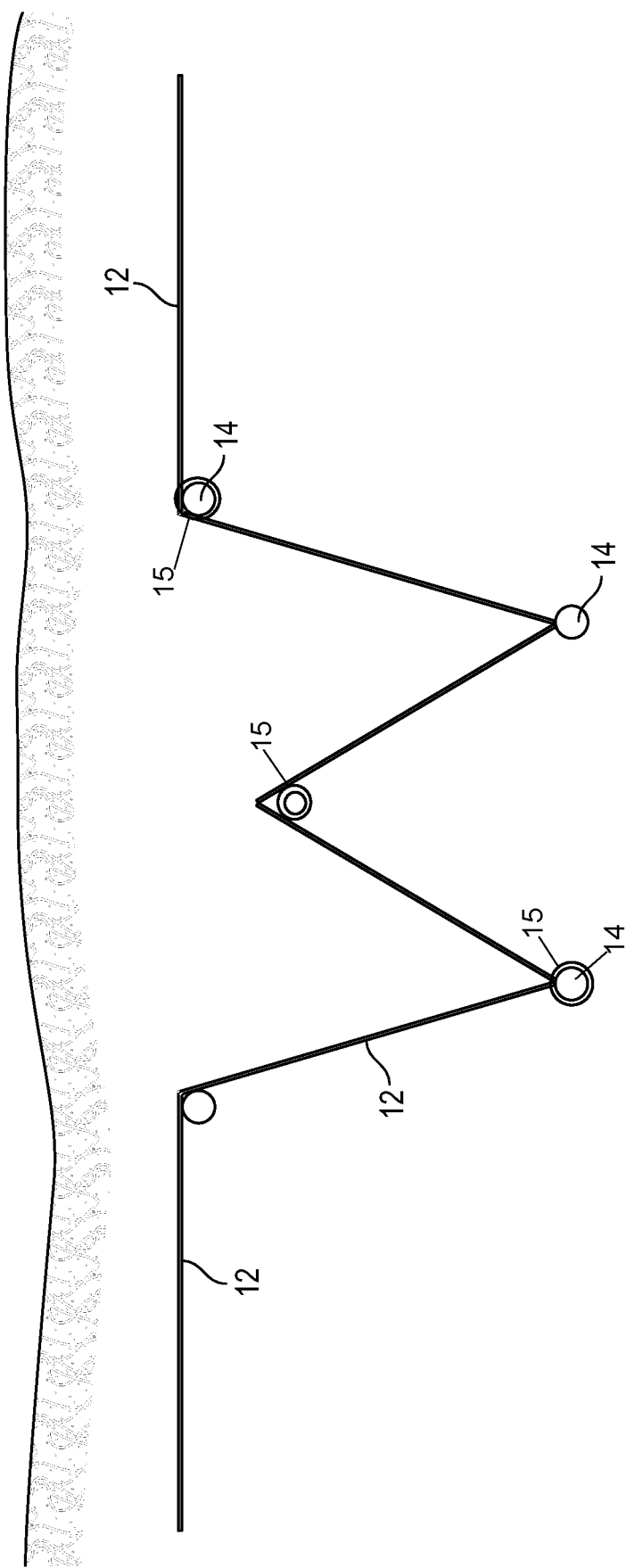
FIG. 7 is an elevational view of a mid-peak pleated seed carrier, in accordance with features of the present invention.

When fully expanded, the device may be 3-5 cm wide, for example if a mid-peak configuration (FIG. 7) of the device is utilized. FIG. 7 represents the ability to expand the width of the radiation field from about 2 cm to multiples thereof, for example 6 cm, assuming ½ cm margins. For example, the inner panels e.g. the upside down "V" of the W may be ½ cm and the outside 1 cm. Or the upside down V maybe 1 cm in diameter and the outside diameter (between the cliffs) may be 2 cm. It should be noted that FIG. 7 depicts the seeds as 14. Alternatively, the seeds may reside in tubes 15 positioned along the peaks and valleys of this invention, such that the ends of the tubes are depicted in FIG. 7.

As such, the device width expands as much as 3-fold from its folded configuration (FIG. 1) to its fully deployed configuration (FIG. 2).

In an embodiment of the invention, bumpers 18 may be placed on the underside of the pleated sheet so as to keep the entire sheet from folding into too compact a construct. For example, the bumpers provide a means for preventing underside, opposing faces of the pleated structure from contacting each other. (Other means for preventing opposing sheets contacting each other may include a natural outwardly directed or spring bias to the material 12 used as the substrate.) Generally, the bumpers may be comprised of a convenient material, such as aluminum, lead, or a composite material within which is mixed large barn materials for attenuation.

Also, if the bumpers are located about 0.25 cm from radiation sources, then the bumpers need only be about 2 mm in length (i.e., extending 2 mm from their proximal end at which they are anchored to the substrate 12.) As such, the bumpers serve as additional attenuation substrates wherein the radiation passes through the bumpers prior to impinging on mucosa and/or tissue to be treated.

In a first configuration, the carrier may be positioned within the body in its contracted, undeployed mode. Deployment of the carrier may be done manually, by the clinician. For example, the inventor envisions massage or manual manipulation of the pleated substrate as a means for activating expansion activators initially placed into the carrier.

Alternatively, deployment may occur via any number of environmental cues, such as body temperature, pH, moisture, plasma- or lymph-delivered activating agents (such as water, nanoparticles), or remotely applied stimuli such as externally applied magnetic, electromagnetic radiation, and combinations thereof.

Figure 3:
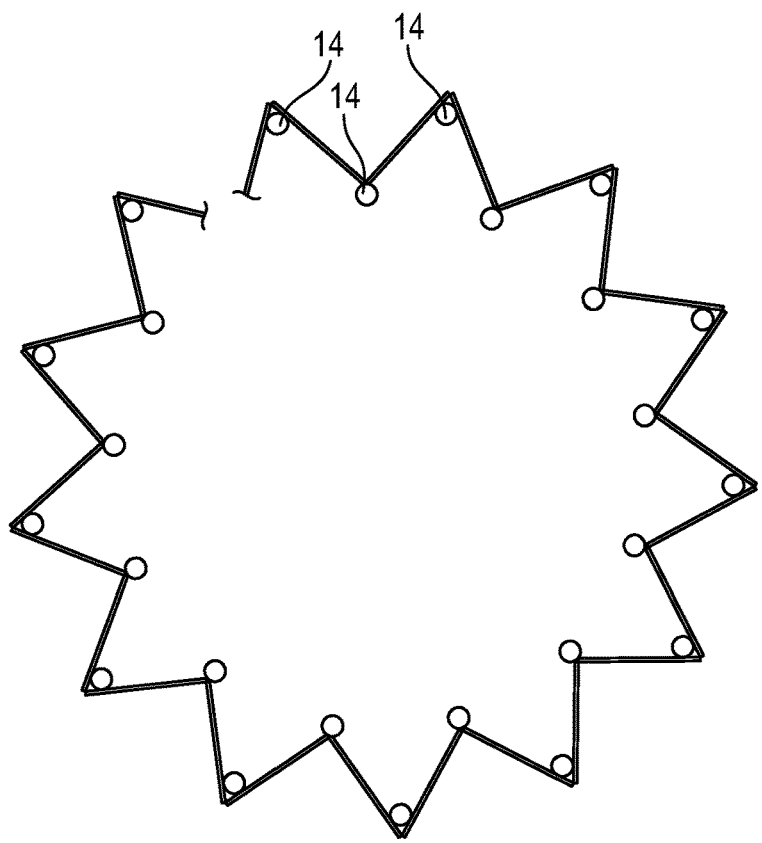
FIG. 3 is side view of the pleated seed carrier configured in a circle, in accordance with features of the present invention.
Figure 4:
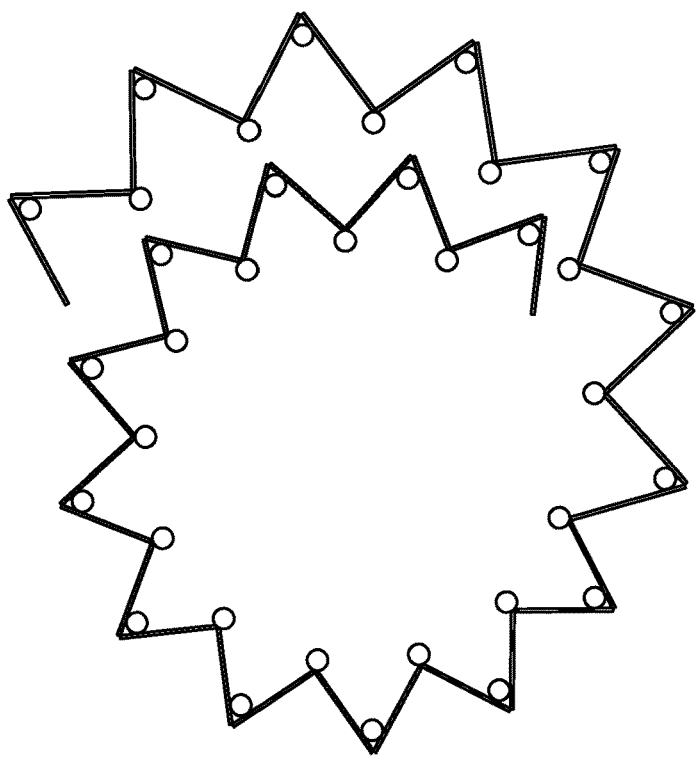
FIG. 4 is a side view of an overlapping, pleated seed carrier configured in circle, in accordance with features of the present invention.

FIGS. 3 and 4 depict an embodiment of the invention folded upon itself. This allows for variation in radial dimensions. For example, FIG. 3 shows a fully expanded construct in spherical mode, thereby conferring maximum cross section "d" to the construct. FIG. 4 shows the construct overlapping at its ends, thereby presenting a construct with a smaller cross section. The overlap may enhance filtering of radiation, particularly if the seeds 14 are supported by the interior facing surface of the circle, as shown in FIG. 3. More than one sheet may be used to produce the circular configuration, depending in on the elasticity of the support material 12 utilized.

The spherical expansion and contraction may be controlled by the substrate's 12 interaction with various environmental stimuli in vivo, such as pH of physiological fluids, body temperature, and medicaments circulating through the body. Expansion and contraction may also be effected by body movements, such as peristalsis, breathing, and voluntary movements. Aside from arranging the substrate as a cylinder, the substrate may be arranged as a cone, have a first superior end 20 defining the apex of the cone, and a second depending end 22 defining the base of the cone. Depicted as FIG. 8, the cone's apex or first superior end would define overlapping portions of opposing edges of the substrate. Conversely, the base of the cone 22 would form a circle. This sort of configuration may be used in treating neoplasms of the breast parenchyma, the bladder parenchyma, the kidney parenchyma, or the liver parenchyma.

Figure 8:
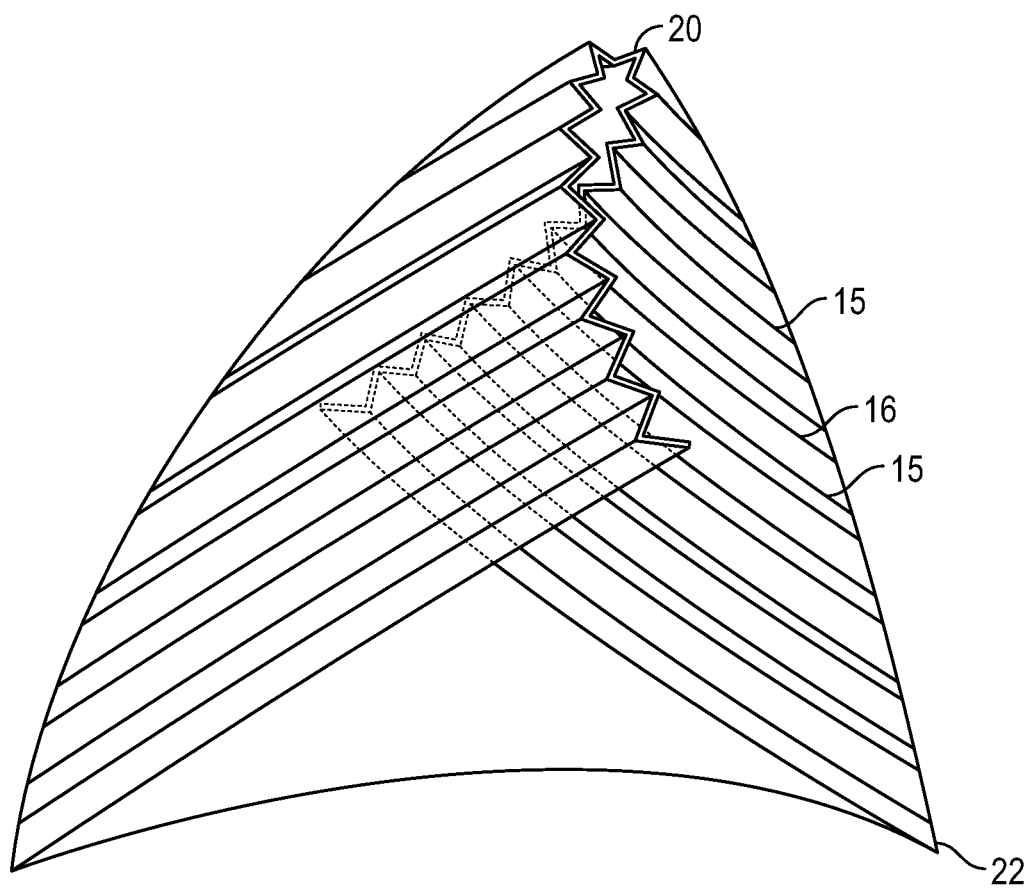
FIG. 8 is a schematic elevational view of a pleated substrate arranged as a cone, in accordance with features of the present invention.

In addition, the cone as depicted in FIG. 8 may be joined at its base end 22 with the base end of another cone to form a spheroid, such that the conjoined bases define an equator of the sphere.

FIGS. 9A-9C depict another configuration of a spherical vehicle, wherein individual leaves 30 are circularly arranged along the periphery of a flat, circular plate 32. As in FIG. 8, this circular plate 32 may be joined with another similarly configured vehicle to form a sphere.

As depicted in FIG. 9, each of the leaves have a first proximal end 34 in hinged communication with the periphery of the plate, and a second distal end 36 in slidable communication with the distal ends of adjacent leaves. As depicted in FIG. 9, a middle leave is positioned between two flanking leaves. The middle leaf overlaps one of the distal ends of the first flanking leaf and simultaneously is overlapped by the second flanking leaf. This results in a concerted opening and closing of the sphere during its radial expansion and contraction. In the closed, undeployed configuration (FIG. 9A), the aperture 41 forming at the apex (and depending end of the bottom structure) is preferably less than 1 centimeter in diameter so as to avoid therapeutic "cold spots."

This embodiment is shown with tubes 42 positioned on outwardly facing surfaces of the leaves. These tubes are adapted to receive radioactive seeds. Aside from tubes, seeds may be directly attached to the outwardly facing surfaces of the leaves. Alternatively, or in addition, the side edges 38 and distal ends 40 of the leaves may be lined with seeds. As the leaves open or close by their rotation about the plate 32, seeds lining distal portions of the leaves may be exposed or covered by edges of adjacent leaves. This provides a means for attenuating dosage during collapse of the leaves. As noted in FIG. 9, the dashed lines connote underlying substrate edges, those dashed lines less prominent, and therefore dose shielding not as present, as larger regions of the leaves are opened FIG. 9C to the surroundings in full deployment mode, compared to in full contraction configuration FIG. 9A.

As such, FIG. 9 depicts a carrier of radioactive particles for brachytherapy, the carrier comprising a base defining a center region and a periphery; a plurality of leaves, each of said leaves defining a first proximal end hinge-ably attached to the periphery of the base, a second free distal end, and side edges extending from the first end to the second end; and radioactive seeds positioned along the side edges.—

The carrier defines the first un-deployed configuration (FIG. 9A) wherein the distal ends of the leaves point toward the center of the base. In this configuration, one of the side edges of a first leaf overlaps about half of an adjacent leaf.

The carrier also defines a second deployed configuration (FIG. 9C) wherein the distal ends of the leaves extend beyond the periphery of the base. In this configuration, one of the side edges of a first leave over-lap an edge of an adjacent leaf. When the base is circular, the distal ends of the leaves define an aperture coaxial with the center region of the base. FIG. 9B depicts this embodiment in a partially deployed configuration.

As discussed above, the distances between the peaks 15 and valleys 16 should approximate 1 cm. These structures, due to the pleated nature of their constituent substrates, may expand radially along cross section d.

Figure 5:
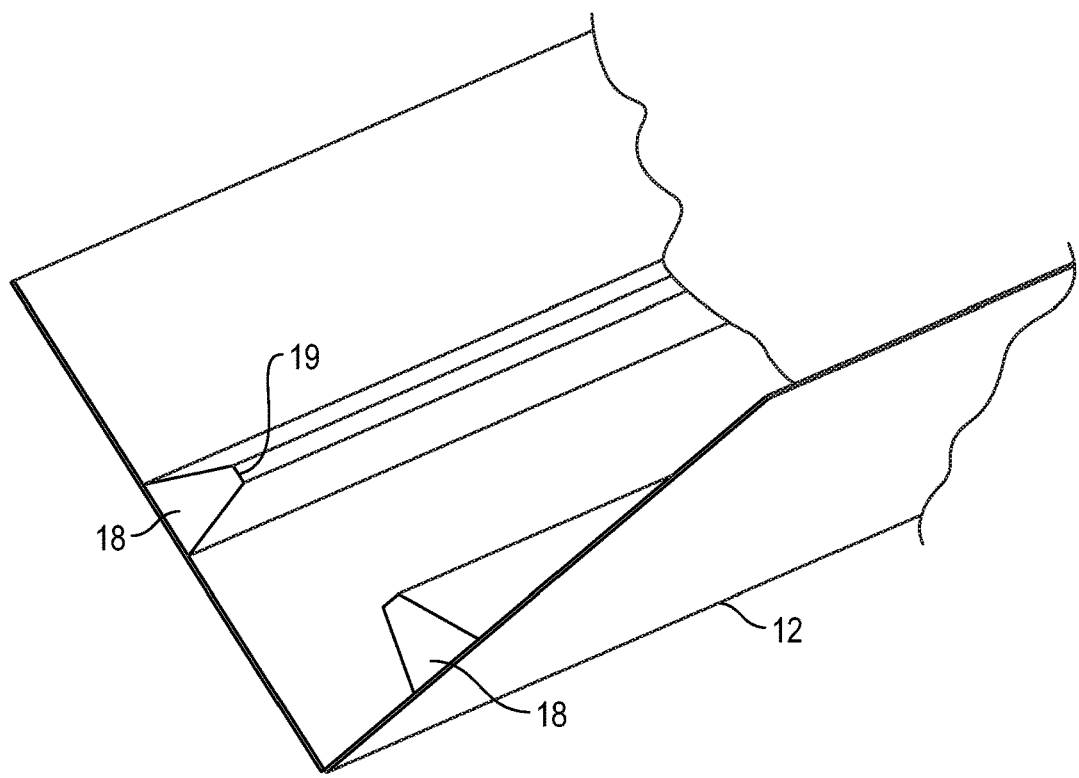
FIG. 5 is a schematic perspective view of a pleated seed carrier in partial deployment, in accordance with features of the present invention.
Figure 6:
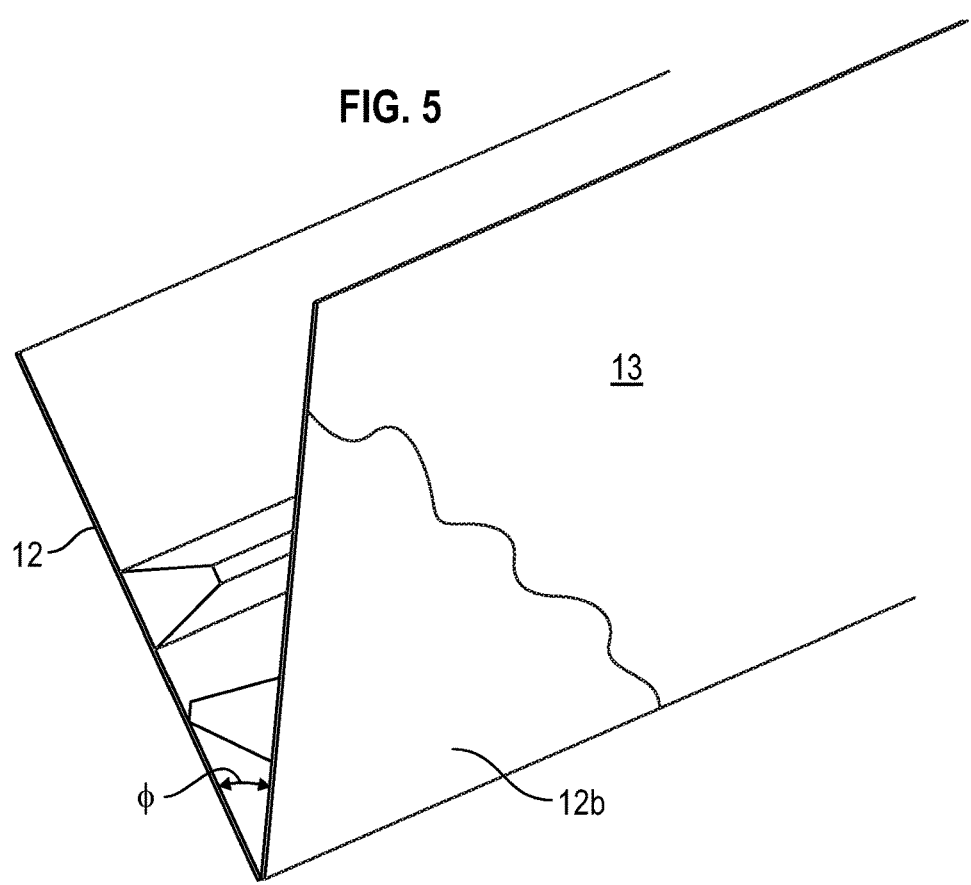
FIG. 6 is an schematic perspective view of a pleated seed carrier in collapsed configuration, in accordance with features of the present invention.

FIG. 5 is an elevational view of a schematic depiction of the device. Unlike the bumpers 18 depicted in FIG. 1, the bumpers 18 are shown offset from each other so that the distal tips 19 of each do not contact each other when the structure is completely collapsed, as shown in FIG. 6. Rather, the distal tips 19 of each bumper contact the opposing surface of the substrate to prevent the opposing surfaces from contacting each other. In this configuration shown in FIG. 6, the angle Ø formed by the opposing surfaces ranges from about 25-40 degrees. This provides a means for separating each lane of seeds in adjacent peaks or valleys to a consistent distance of between 0.75 and 1.5 cm, and preferably about 1 cm. The bumpers may be comprised of any convenient material, for example aluminum, stainless steel, or other relatively inert yet radio-opaque material. Radiation transparency will be determined based on the isotope employed such that radio-opacity may not be a requirement for bumper constituent choice.

Carrier Detail

Preferably the pleated substrates are nonallergenic in nature and bacterially/virally sterile. The texture and feel of the substrates may be similar to normal tissue. They may be comprised of radiopaque materials, or may be comprised of radio transparent materials, and ranges of transparency therebetween, depending upon the application and the need for visualization of the seeds. A preferred embodiment is where the RDC was less radio opaque than the radiation seeds so that the seeds within the RDC can be visualized. As noted supra, shape memory polymers having a biased toward deployment or even contraction may be utilized.

Suitable substrates for RDCs include biocompatible materials as plastic ceramics, polycarbonate ceramic, silicone substrates, foam, nitinol, and combinations thereof. Optionally, these biocompatible carriers are absorbed by the body over time. However, the stents comprised of these corrugated configurations may be fabricated to reside permanently in the body.

Also, carrier substrates are utilized which facilitate rapid heat transfer. Construction of the pleated configurations can take several conventional methods, including simply pleating or folding a webbing of the material into alternate peaks 15 and valleys 16. The peak and/or valley regions may define occasional apertures or slits extending along the peaks and/or valleys to facilitate pleating. Also, the apertures may provide a means for drainage or fluid exchange, akin to weep holes.

Alternatively, separate panels 12 may be combined via heat welding, adhesive or other biocompatible joining means. The radioactive particles may be interposed between abutting panels, either via adhesive, or slidably received by sleeves formed by the abutting panels.

The surfaces 12 of the pleated device are chosen based on their relative inertness. As such, plastic, glass, and titanium, are all suitable choices. Generally, the sizes of the device will vary. However, typical sizes are those able to pass through a 12-14 G trocar.

Generally, tumor resection cavities are suitable cancer venues for application, those venues including the kidneys, esophagus, brain meninges, lung masses, nodes, prostate, bladder, uterus, ovary, peritoneal cavities and plural cavities.

The RDC-seed composite is fabricated so that the surface dose of the composite is fairly uniform. This will help with dosimetry when calculating dosages.

In instances of vLDR applications (wherein low energy seeds are utilized) the seeds are placed close to the surface of the carrier (e.g., within about 0.1 to 1 cm, and preferably within about one half of a centimeter.) In an embodiment of the invention, an inert spacer (either radio transparent or radio-opaque) occupies the center of the treatment volume and is surrounded by radioactive RDCs.

Medicament Detail

A myriad of medicaments are envisioned for use in combination with the RDC. Medicament types include radioactive substrates such as brachytherapy seeds, and radioactive fluids. Suitable radio isotopes for permanent seed applications include, but are not limited to, I 125, Pd 103, Cs 131 and Yb 169. All of these sources discharge low energy photons (e.g., from 22 keV to about 100 keV). The range of the radiation depends on geometry especially inverse square law but also adsorption in tissue and air. Individual seeds are shielded by the encapsulation process which usually limits the useful exposure to a short range of undesirable radiations. The initial dose rate would vary inversely with halve life. As an example the typical initial dose rate for an I 125 prostate implant would usually be about 0.07 Gy/hr (7 rad per hour as opposed to about 20 for Palladium 103. Host factors such as oxygenation, intrinsic radiosensitivity proliferation rate repair capacity are more difficult to control.

A suitable brachytherapy seed is available from a myriad of commercial sources, including the Proxcelan™ Cesium 131, manufactured by IsoRay Medical in Richland Wash. Generally, such radioactive particles are provided non-sterile and must therefore be sterilized prior to insertion into the carrier. As such, preferably, the carrier is also capable of being sterilized.

Also as noted supra, the carrier is adapted to receive medicaments. In an embodiment of the invention, the carrier/medicament composite structure is a vehicle for treating cancers and areas of the body invaded by neoplasms. A myriad of radioactive particles are suitable medicaments for being supported by the carrier. Exemplary such particles include, but are not limited to, isotopes such as currently available $^{125}$I, Ytterbium-169, Palladium-103, or Cesium-131 (e.g., Cs half-life=10 days). $^{125}$I is a suitable source for vLDR applications, given its relatively short half-life (about 60 days) and relatively low energy (about 30 keV).

Generally, suitable medicaments are those that are capable of being supported by the carrier. Interaction between the medicament and the carrier can be via adsorption, hydrophilic or hydrophobic interaction, covalent attachment, ionic attachment, or even via adhesive in the case of radioactive particles. Also, the carrier may be combined with radioactive material via bombardment with a radioactive ion.

In an embodiment of the invention, the seeds themselves are not provided in raw state, but rather jacketed in radio-transparent material such as titanium, platinum, tungsten steel, alloys thereof, and combinations thereof. Decay products such as alpha particles, beta particles, auger electrons, Internal Conversion electrons, x rays, and gamma rays are mostly absorbed by the seed encapsulation within the sleeves, and additionally, by the bumpers as described supra.

Often, the radioactive material is adsorbed onto an inorganic substrate, such that the substrate and the radioactive seeds are both encased in the radio-transparent material. Also, radioactive seeds may be separated from each other by the structure of the carrier.

Currently, suitable radioactive particle sizes are those which can be loaded into the RDC. Suitable seed sizes are from 0.4 mm x 4 to 0.8 mm×4 mm. An exemplary sized seed is a 0.8 mm×4 mm seed of Iodine-125 from GE/Oncura. (Iodine seeds may be clad in platinum to filter out alpha particles.) Ytterbium-169 particles from SPEC also are suitable. These dimension ranges define both linear and spheroid shapes.

Typical particle (e.g. seed) diameters and lengths range from about 0.4 to about 1.2 mm in diameter and 0.4 to 1.2 mm in length. Smaller size particles allow for easier placement of the instant invention in small-volume lumen, such as the biliary tract of the liver.

The seeds may be added to the carrier individually or else first chained together and added to the carrier. Generally, the seeds range in size from about 4 mm to 15 mm in length, preferably from about 4 to 8 mm, and most preferably about 6 mm. An embodiment of the invention is where the carrier completely encapsulates the seeds.

The instant invention is not limited to the use of radioactive particles. Pharmaceuticals including radio-pharmaceuticals, dissolvable solids, capsules containing liquid drugs, or other desired material may be included within the RDCs. These medicament particles or materials may also be separated by spacers to provide and maintain the geometry and dosage of the medicament, according to clinical need. For example, if a drug solution is to be applied to a desired portion of the tissue, then a drug delivery particle may be localized to this region by inclusion of spacers for the remaining volume of the carriers.

Other medicament types include antibiotics, chemotherapeutic agents, coagulants, thinners, biologics, and constituents of these medicament types. As the porous carrier is in fluid communication with blood, lymph, and other fluids circulating through the body, medicaments attached to the carrier can be activated by agents delivered via natural fluid transfers of the patient. RDCs can be porous in nature to facilitate fluid transfer through the RDCs is disclosed.

The term medicament need not be restricted to therapeutic materials, but also materials for other clinical purposes. For example, the tubular members may comprise radiopaque substrates that allow for diagnostic imaging of the location of the tubular members or patient anatomy. Specifically, the instant device may be modified to deliver medicaments such as radiopharmaceuticals, radiotracers, or contrast agents for possible applications such as Computed Tomography (CT), Single Photon Emission Computed Tomography (SPECT), or Magnetic Resonance Imaging (MRI). A focalized application of such medicaments may be desirable for diagnostic imaging or other clinical applications because the substance may be at a desired local concentration without unnecessary exposure of non-target areas such as occurs with systemic administration.

Other medicaments that may be used with the instant device include but are not limited to small interfering RNA (siRNA), DNA used for gene therapy, monoclonal antibodies targeted to relevant receptors, growth factors such as the Insulin-like Growth Factors (IGFs), radiolabeled nanoparticles, or medicaments which are chemically targeted to desired tissues or areas, for example, botulinum toxin type A which is the active ingredient in botox.

In operation, a substrate is positioned within a treatment site (for example: endoscopically, surgically, via injection, or a combination of these modalities). The substrate may be positioned fully retracted, partially deployed or fully deployed (e.g., expanded to full width) depending on the space available. As noted surpa, simultaneous contraction or deployment occurs depending on patient movement, and in situ physiological factors such as plasma pH, patient body temperature, hydration levels, etc.

Generally the pleated scaffold need not be harvested inasmuch as the device comprises biocompatible materials.

A myriad of neoplasms are treated with the invented device, including post renal lumpectomies, post liver and bone metastases, post pancreatic resections, sarcomas, transurethral resections, and bone cysts.

EXAMPLE

A preferred embodiment is the use of shaped soft tissue equivalent carriers in which a permanent radioactive seed is centrally spaced (or otherwise optimally spaced viz the effected tissue). Palladium and Iodide seeds are attractive commercially available radio isotopes. The seeds placed in such a carrier are usually homogeneously (i.e. evenly) spaced when subsequently placed within a target volume. Bunching of sources in a specific area and other volumes in which there is a paucity of sources is avoided.

A suitable material would have similar consistency of the normal tissue it is replacing (such as breast), and be hypo allergenic. This material would not leak and would have an appropriate geometry. Also, the RDC defines a shape similar to the dose pattern of the radioisotope seed utilized. This prevents over exposure and uneven dosages to the tissue requiring treatment.

Spacers comprised of inert material can be used to separate and or link seeds together. The spacers provide a means to maintain the desired geometry of the radioactive particles relative to each other, and to the tissue being treated. The spacers may be free flowing and radio opaque to serve as a diluent, or else radio-transparent and attached to the particles flanking them, those flanking particles being radioactive particles, additional spacers or combinations thereof. These spacers may include markers or other nonradioactive materials such as metals (e.g., gold, other nonferrous material, ferrous material), nonmetals (e.g., plastics, fluidized chemical moieties) which can be further used to modify the plume of radiation emanating from the seed, and also to assist in determining the position of implanted radiation sources relative to each other, to the marker, and to the original tumor site.

The markers may comprise sutures, particles homogeneous dispersed within the radioactive source, capsulized fluids (scintillation fluids), and discrete objects and shapes placed at predetermined points either on or within the RDC or tumor excise site. In one embodiment, the markers are placed as staples, which typically define a periphery of a tumor excise site.

The diameter of the RDCs and the sizes of the particles contained therein will be constrained by the volume of the target lumen. As such, the diameter will be empirically determined upon receiving imaging data as to actual structural size of the effected tissue. Often the distance between the outside surface of the RDC and the margins of the tumor site (where healthy tissue is found) is between about 0.5 and about 1 centimeter. Upon first inserting the RDC, this distance is accurately determined and compared at a subsequent time to determine if any movement within the body or within the excision site, has occurred. Methods for imaging movement include CT scans, Geiger counters, x-rays, fluorescence induced by radiation including magnetic fields, visible light, IR- and UV radiation, radio-frequency radiation, alpha-, beta-, and gamma-radiation. The sources may be left in place permanently in some instances and removable in others.

An endoscope can be used to load or replace the radioactive particles in situ by delivering the radioactive particles through a delivery catheter or loading tool. The endoscope is also used to deliver other medicaments such as drug solutions by use of a delivery catheter or loading tool.

The radioactive particles may be removed or replaced according to therapeutic need. For example, the tumor may shrink or change its shape or the carrier's position may migrate in situ. The position of the radioactive particles relative to the target tissue can be adjusted by changing the order and position of the spacers and radioactive particles in situ at a later time after device insertion. Alternatively, if the reversibly deformable material contains ferrous material, the carrier may be manipulated by an externally applied magnetic field. Marginal recurrences are relatively common and application of a second stent may address these eventualities.

A variety of shielding material may be included at one surface of the RDC so as to prevent undesired radiation exposure of certain tissue. Suitable examples of materials include Pb, Al, Ti, W or combinations/alloys of these elements. In the case of lead, shielding thicknesses may range from about 0.1 mm to about 0.5 mm, and typically about 0.25 mm, and result in attenuating Iodine-125 by half. In one embodiment, the shielding material may be attached to the RDC. In other embodiments, the shielding material may be attached to one side of the radioactive particles or amalgam of particles. This shielding material may be used to prevent exposure of healthy or other tissue in which it is not desirable to expose the tissue to radiation.

The instant invention may comprise modifications to facilitate the placement and removal of medicament particles. In one possible embodiment, brachytherapy particles and spacers may be coated, for example with wax or silicone, to allow easier translocation into and out of the RDCs. In another embodiment, the RDCs may be reinforced with additional elements to maintain their shape, and keep their hollow center open in instances where medicament is arranged around those centers.

The present invention prevents hotspots by maintaining a more consistent distance between the radiation source and the tissue wall. Thus, the invention enables a vLDR source attached to a RDC, where the radiation source is held on the periphery of the carrier to conform to anatomical curvatures. Thus, large deviations in distance between the tissue and the radiation source do not occur. Additionally, tumors of longer length can be treated with a vLDR source attached to a RDC.

If hot spots are unavoidable because of geometry, the deformability of the carrier allows placement of the hot spots within a tumor. The invention provides a system of treating the metastasis site but without exposing healthy surrounding tissue with permanently embedded radiation sources. In this embodiment, a radiation source is attached to or placed within a RDC which is expanded against the lumen wall, wherein the geometry of the radioactive particles is determined and preserved by separation of the particles with spacers. This would allow for particle position to be customized to maximize delivery to the tumor and minimize exposure to healthy tissue.

Three dimensional configurations of a tumor are ascertained by imaging and the precise position of loose or connected radioactive particles is calculated based on desired radioactive dosages in three-dimensional space. Details for such imaging are known and can be found in Langley et al, 2012, BJU International, 109, 1-6, the entirety of which is incorporated by reference. The use of these methods to determine particle position within tubular members positioned against the inner wall of a body cavity, such as a vertebral cavity during kyphoplasty, allows for a customized delivery of radiation, representing a significant improvement of delivery of radiation to tumors located on the wall of endoluminal spaces. Particle activity and position can be calculated based on information from imaging (such as X-ray or CT scans) or other means.

The invention provides a system whereby a removable vLDR radiation source is attached to a RDC, wherein the radiation source can be left in the patient for longer periods, and can be removed or replaced if required. The ability to removably position vLDR radiation sources via expandable carriers confers advantages over current HDR methods using a central catheter, as 1) the vLDR source would be held in direct apposition to the target tissue by the stent, 2) it could be left for an extended period of time in the patient, and 3) the radiation source could be potentially removed and replaced according to clinical requirements, for example changes in tumor shape and size. If after a length of time the radiation emanations are so weak, the seeds may potentially not need to be removed. Additionally, the presence of a vLDR source would improve the mechanical relief of dysphagia by the RDC, as the vLDR would prevent the tumor from growing over the carrier. The proposed device would allow for a potentially removable vLDR radiation source that could be replaced by relatively non-invasive surgical means, such as endoscopy.

The present invention can be applied to can involve any or all medical conditions discussed above in various combinations, as desired. Accordingly, it will be readily apparent to the skilled artisan that in some of the disclosed methods certain steps can be deleted or additional steps performed without affecting the viability of the methods.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," "more than" and the like include the number recited and refer to ranges which can be subsequently broken down into subranges as discussed above. In the same manner, all ratios disclosed herein also include all subratios falling within the broader ratio.

One skilled in the art will also readily recognize that where members are grouped together in a common manner, such as in a Markush group, the present invention encompasses not only the entire group listed as a whole, but each member of the group individually and all possible subgroups of the main group. Accordingly, for all purposes, the present invention encompasses not only the main group, but also the main group absent one or more of the group members. The present invention also envisages the explicit exclusion of one or more of any of the group members in the claimed invention.

The embodiment of the invention in which an exclusive property or privilege is claimed is defined as follows:

1. A device for brachytherapy comprising: a substrate having a longitudinal axis and a latitudinal axis, wherein the substrate comprises alternating peaks and valleys which are parallel to the longitudinal axis, the alternating peaks and valleys defining latitudinally extending pleats; and a plurality of medicament moieties positioned on the peaks and valleys of the substrate, and further comprising longitudinally extending bumpers positioned on the substrate between the peaks and valleys.

2. The device as recited in claim 1 wherein the bumpers are radio-opaque.

3. The device as recited in claim 1 wherein a first proximal edge of the bumpers are attached to the substrate and a first distal edge of the bumpers oppose an adjacent pleat.

4. The device as recited in claim 3 wherein the bumpers prevent adjacent pleats from contacting each other.

5. The device as recited in claim 3 wherein the bumpers are positioned on opposing surfaces of a pleat.

6. A carrier of radioactive particles for brachytherapy, the carrier comprising
   a) a base defining a center region and a periphery;
   b) a plurality of leaves, each of said leaves defining a first proximal end hinge-ably attached to the periphery of the base, a second free distal end, and side edges extending from the first end to the second end; and
   c) radioactive seeds positioned along the side edges.

7. The carrier as recited in claim 6 wherein the carrier defines a first un-deployed configuration when the distal ends of the leaves point toward a center of the base and one of the side edges of a first leaf from each of said leaves overlap the edge of an adjacent leaf.

8. The carrier as recited in claim 7 wherein one of the side edges of the first leaf overlap about half of an adjacent leaf.

9. The carrier as recited in claim 7 wherein the base is circular and the distal ends of the leaves define an aperture coaxial with the center region of the base.

10. The carrier as recited in claim 6 wherein the carrier defines a second deployed configuration when the distal ends of the leaves extend beyond the periphery.

11. The carrier as recited in claim 10 wherein one of the side edges of a first leaf from each of said leaves over-lap an edge of an adjacent leaf.

* * * * *